US008998984B2

(12) United States Patent
Phillips (10) Patent No.: US 8,998,984 B2
(45) Date of Patent: Apr. 7, 2015

(54) ADJUSTABLE TORIC INTRAOCULAR LENS

(71) Applicant: Andrew F. Phillips, La Canada, CA (US)

(72) Inventor: Andrew F. Phillips, La Canada, CA (US)

( * ) Notice: Subject to any disclaimer, the term of this patent is extended or adjusted under 35 U.S.C. 154(b) by 124 days.

(21) Appl. No.: 13/740,547

(22) Filed: Jan. 14, 2013

(65) Prior Publication Data

US 2014/0200666 A1 Jul. 17, 2014

(51) Int. Cl.
*A61F 2/16* (2006.01)
*A61F 9/008* (2006.01)

(52) U.S. Cl.
CPC .............. *A61F 2/1627* (2013.01); *A61F 2/1629* (2013.01); *A61F 2002/1645* (2013.01); *A61F 9/00804* (2013.01); *A61F 9/00821* (2013.01); *A61F 9/00827* (2013.01)

(58) Field of Classification Search
USPC ....................................... 623/6.34, 6.37, 6.46
See application file for complete search history.

(56) References Cited

U.S. PATENT DOCUMENTS

| | | | |
|---|---|---|---|
| 4,575,373 A | 3/1986 | Johnson | |
| 5,571,177 A | 11/1996 | Deacon et al. | |
| 5,728,155 A | 3/1998 | Anello et al. | |
| 5,843,188 A | 12/1998 | McDonald | |
| 5,964,802 A | 10/1999 | Anello et al. | |
| 6,013,101 A | 1/2000 | Israel | |
| 6,443,984 B1 | 9/2002 | Jahn et al. | |
| 7,210,783 B2 | 5/2007 | Jethmalani et al. | |
| 7,837,326 B2 | 11/2010 | Jethmalani et al. | |
| 8,182,531 B2 | 5/2012 | Hermans et al. | |
| 2002/0128710 A1 | 9/2002 | Eggleston | |
| 2003/0135271 A1 | 7/2003 | Bandhauer | |
| 2004/0162612 A1 | 8/2004 | Portney et al. | |
| 2005/0182489 A1 | 8/2005 | Peyman | |
| 2007/0299487 A1 | 12/2007 | Shadduck | |
| 2011/0166652 A1 | 7/2011 | Bogaert et al. | |

FOREIGN PATENT DOCUMENTS

| | | |
|---|---|---|
| WO | WO 2010/062976 | 6/2010 |
| WO | WO 2010/125596 | 11/2010 |
| WO | WO 2011/151215 | 12/2011 |

OTHER PUBLICATIONS

The Correction of Astigmatism During Cataract Surgery with Toric Intraocular Lenses, Lane S. et al., Cataract Surgery, Ch. 39, p. 469-475, Elsevier (Third Ed., 2010).

(Continued)

*Primary Examiner* — David H Willse
*Assistant Examiner* — Tiffany Shipmon
(74) *Attorney, Agent, or Firm* — Gordon & Jacobson, PC (57) ABSTRACT

An adjustable astigmatism-reducing intraocular lens includes a toric optic with a long axis. The optic is rotationally coupled to haptics, and a plurality of struts extend between the optic and the haptics. The struts are held under tension and individually releasable via laser, or are heat shrinkable to increase the tension of selective struts. When a strut is released or shrunk, a torsional force is applied to angularly adjust the optic relative to the haptics. After the lens has been implanted and healed relative to the tissue, struts are individually released via laser ablation to cause torsional instability and resulting net rotational adjustment, or individually heat shrunk to tension the strut, to cause torsional instability, and effect net rotational adjustment to ensure that a long axis of optic is aligned with the axis of astigmatic correction of the eye.

20 Claims, 5 Drawing Sheets

(56) References Cited

OTHER PUBLICATIONS

Surgical Correction of Astigmatism During Cataract Surgery, A.T. Comez et al., Astigmatism—Optics, Physiology and Management, 2012, Chapter 17, pp. 293-308, available at www.intechopen.com/books/astigmatism-optics-physiology-and-management/correction-of-astigmatism-during-cataract-surgery.

Toric Intraocular Lenses in Cataract Surgery, N. Visser et al., Astigmatism—Optics, Physiology and Management, 2012, Chapter 16, pp. 265-292, available at www.intechopen.com/books/astigmatism-optics-physiology-and-management/Toric-intraocular-lenses-in-Cataract-Surgery.

Astigmatism Correction in Cataract Surgery with Rayner Toric Intraocular Lenses, S.L. Painter et al., Clinical Optometry 2010:2 79-84.

Starr Toric Silicone Single Piece IOL, STARR Surgical, STARR Toric, Downloaded Sep. 19, 2012, Available at https://www.staartoric.com/?region=us.

AcrySof® IQ Toric IOL Taking Precise Astigmatism Correction to the Next Level, Downloaded Sep. 19, 2012, Available at https:/www.alconsurgical.com/Innovation-In-Action-aspx.

Cataract Surgeons Strive for Perfection in Postoperative Visual Outcomes, Ocular Surgery News, Apr. 21, 2012, available at www.healio.com.

Light Adjustable Lens, Refractive Results Equal Corneal Laser Surgery at 24 months; Near Vision Improved, Howard Larkin, Cataract & Refractive, Eurotimes, vol. 17/18, Issue 12/1, Dec. 2012.

ADJUSTABLE TORIC INTRAOCULAR LENS

BACKGROUND OF THE INVENTION

1. Field of the Invention

The present invention relates to intraocular lenses, and more specifically intraocular lenses having astigmatic correction. More particularly, the present invention relates to an intraocular lens in which the optic can be angularly adjusted relative to the haptics to thereby adjust the axis of astigmatic correction following implantation.

2. State of the Art

The cornea of a perfectly shaped eye has a smooth circular surface, like a sphere. Corneal astigmatism is a common condition in which the eye's cornea has an irregular, oblong shape causing a refractive error resulting in distorted vision. The condition, if requiring treatment, is often treated with corrective lenses such as eyeglasses or contact lens or laser refractive surgery (laser in-situ keratmileusis (LASIK) or photorefractive keratectomy (PRK)).

While corneal astigmatism is often treated with corrective lenses or laser refractive surgery, corneal astigmatic patients having cataracts and undergoing surgery to replace the cataract lens with an intraocular lens (IOL) can request the implantation of a toric intraocular lens adapted to treat their corneal astigmatic condition during their lens replacement surgery. Toric lenses must be implanted along a prescribed rotational axis of correction such that the optical correction designed into a lens is directed along the correct rotational axis to properly treat the distortion. It has been noted that critical to the success of a toric IOL is its rotational stability in the capsular bag; for every degree of misalignment off the desired axis there is a 3 percent loss of cylinder correction. Lane S. et al., The Correction of Astigmatism During Cataract Surgery with Toric Intraocular Lenses, *Cataract Surgery*, Ch. 39, p. 469-475, Elsevier (Third Ed., 2010). However, not all implantations are successful in achieving the intended rotational alignment. Further, even after a lens has been implanted, there can be an unpredictable degree of rotational shift that occurs during post-operative healing to the capsular remnant which can result in the lens rotating relative to the initial axis of implantation. One study has found that at two weeks post-implantation, at least 38% of the optics had rotated more than 10°, and in some cases had significantly greater rotation off axis. Id. The resulting axial misalignment can reduce or eliminate the desired correction. Moreover, axial misalignment can introduce higher order optical aberrations which are not correctable with glasses.

SUMMARY OF THE INVENTION

An intraocular lens includes an optic having designed therein a lens structure which optically compensates for astigmatism. The optic is preferably a 'toric' optic defined from a periphery of a torus to provide an astigmatic correction. The optic may also be shaped to include any other refractive correction necessary to compensate for aberrations in a patient's cornea, as well as be adapted in structure alone or relative to the haptics to be accommodative or non-accommodative in accord with the principals, features, and structure of such optics and lenses known in the art.

The optic is rotatably mounted on a plurality of haptics. A first portion of the optic is rotationally coupled to a first haptic, a first pair of struts extends preferably under tension between the first haptic and the optic, and the first pair of struts is radially displaced to extend outside the field of view of the optic on opposite sides thereof to apply respective opposing rotational forces on the optic. A second portion of the optic is rotationally coupled to a second haptic, a second pair of struts extends preferably under tension between the second haptic and the optic, and the second pair of struts is radially displaced to extend outside the field of view of the optic on opposite sides thereof to apply respective opposing forces on the optic.

When the optic, the first and second haptics, and the struts are in an as implanted configuration, they preferably form a lens having at least one axis, and preferably two axes of symmetry, with one line of symmetry preferably extending through the axis of correction. As implanted, the tensioned struts extending from the first and second haptics to the optic on each of at least two sides of the optic maintain the lens in a state equilibrium and thus a state of torsional stability. In accord with one aspect of the invention, the struts are post-operatively individually modifiable, by the use of energy, such as a laser heat shrinking or ablation, or by surgeon manipulation, such as by microscissors. In one embodiment, when one of the struts connected to a haptic is removed, a momentary torsional instability is exerted by the other of the struts connected to the same haptic. This results in rotation of the optic relative to the first and second haptics about the optical axis in the direction of greater applied tension by the remaining struts. Then, with removal of a second one of the struts a second momentary torsional instability is exerted by the remaining struts to result in further rotation of the optic relative to the haptics, resulting in a greater amount of rotations. Each amount of rotation is in a predefined direction and predefined amount relative to the first and second haptics. This allows the angular relationship of the optic relative to the haptics to be adjusted post-operatively in four distinct gradations, e.g., +10°, +20°, −10°, −20°, to provide the intended relationship of the optical axis of the optic relative to the astigmatic aberration and thus maximize the correction.

It is appreciated that correction can be provided with the elastic struts attached to one haptic only in the as-implanted configuration. Also, more than two struts can be attached to each haptic to further graduate the degrees of post-operative rotational correction. Further, additional haptics, such as a total of three, four or more, and associated pairs of struts extending between the haptics and optic can be provided to also further graduate the rotational adjustment.

The haptic includes a fixation hole for fixation of the lens to the capsular bag remnant during healing. In one embodiment, the haptic also includes a rotational guide slot and the optic is provided with a pin that rides in the slot. When the lens is in a state of equilibrium, the pin resides at the center of the slot. When a strut is removed, the struts applying an opposing tension force exert sufficient rotational force to advance the pin through the slot and rotate the optic relative to the haptics until the countering struts act under tension to decrease in length and the countering strut is consequently stretched until the net rotational force is zero. The material and diameter of the struts are chosen so that the zero rotational force under such conditions occurs after a predetermined number of degrees of rotation, e.g., 10°. If the remaining countering strut is removed, the opposing tension struts further act under tension to decrease their respective length, advance the pin of the optic through and to the end of the respective guide slot in the haptic, and thereby rotationally displacing the optic by a second defined angle, e.g., 20°. In another embodiment, the haptic can be provided with the pin and the periphery of the optic can define the elongate curved slot which moves relative to the pin.

In a further embodiment of a rotational guide track, the optic can define an at least partially circumferential bead, and the haptic can include a channel through which the bead can rotationally displace. Stops can be provided along portions of the bead to define pre-set amounts of maximum angular displacement. Similarly, in yet another embodiment, the optic can include an at least partially circumferential channel, and the haptic can define a bead over which the channel of the optic can rotationally displace. Stops can be defined within the groove to limit and define pre-set amount of angular displacement of the optic relative to the haptic.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
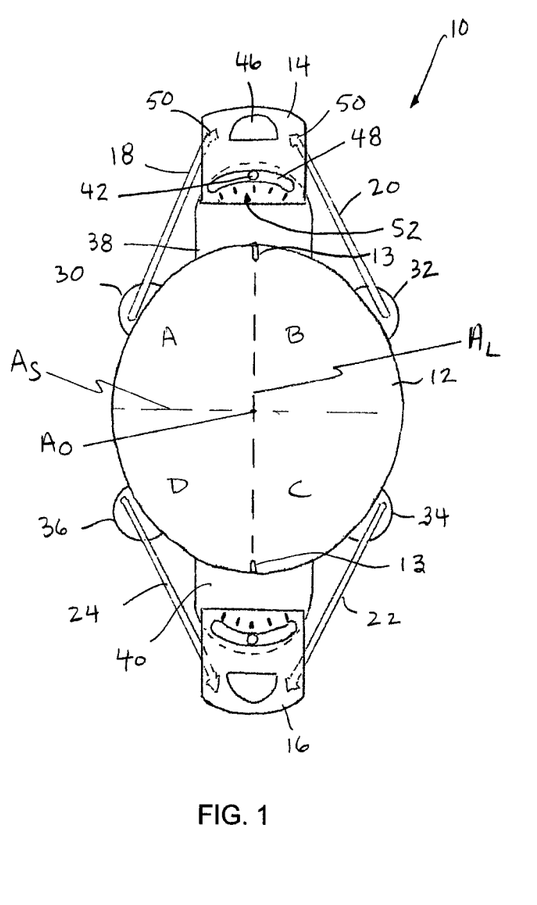
FIG. 1 is a top view of an adjustable toric intraocular lens according to the invention.
Figure 2:
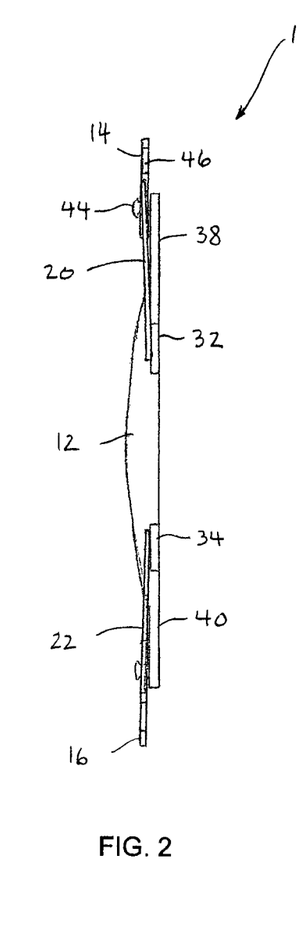
FIG. 2 is a side elevation view of the lens of the FIG. 1.

Turning now to FIGS. 1 and 2, an embodiment of an intraocular lens 10 includes an optic 12 and at least first and second haptics 14, 16, relative to which the optic can be rotated about the optical axis. Tensioned struts 18, 20, 22, 24 are coupled between the optic 12 and the haptics 14, 16 to retain the optic in a state of equilibrium, and thus a state of torsional stability.

The optic 12 is a 'toric' optic having different optical power and focal length in two orientations perpendicular to each other; i.e., across a longer axis AL and a shorter axis AS intersecting at the optical axis AO. When the longer axis AL is aligned with the axis of astigmatic correction, the optic compensates for the corneal astigmatism. The optic is preferably provided with registration marks 13 at each end of axis AL to facilitate proper implantation. In addition to astigmatic correction, the optic 12 may also be shaped to include any other refractive correction necessary to compensate for aberrations in a patient's cornea, as well as be adapted in structure alone or relative to the haptics to be accommodative or non-accommodative in accord with the principals, features, and structure of such optics and lenses known in the art.

The optic 12 is connected to, and preferably unitary with, two pairs of peripheral strut mounts 30, 32, 34, 36 for coupling struts 18, 20, 22, 24 in tension between the optic 12 and the first and second haptics 14, 16. The struts 18, 20, 22, 24 are preferably an elastic construction. The strut mounts 30, 32, 34, 36 are preferably radially displaced off the optic by up to 2 mm, and more preferably approximately 1 mm. However, in an alternate embodiment, the struts mounts are defined at a peripheral edge of the optic. The strut mounts 30, 32 are provided on opposing sides of the longer axis AL and sufficiently spaced away from the first haptic 14 and toward the shorter axis AS of the optic 12 to allow the tensioned struts to exert respective suitable, sizable, and/or determined torsional forces between the optic and the first haptic 14, as described further below. On the opposite side of the shorter axis AS, strut mounts 34, 36 are provided on opposing sides of the longer axis AL and sufficiently spaced away from the second haptic 14 and toward the shorter axis AS of the optic to allow the tensioned struts to exert respective suitable, sizable, and/or determined torsional forces between the optic and the second haptic 16, as also described further below. A first end of each strut 18, 20, 22, 24 is fixed to a respective strut mount 30, 32, 34, 36. Such fixation of strut to strut mount may occur through molding with or other unitary formation with the optic, particularly when the optic is cast. To that end, it is appreciated that only two strut mounts can be provided, each aligned on opposite sides of the shorter axis AS, with struts 18, 24 extending from one mount to opposing haptics, 14, 16, and with struts 20, 22 extending from the other mount to opposing haptics.

Referring to FIGS. 1 and 2, the optic 12 also includes first and second haptic mounts 38, 40 extending outward from diametrically opposing sides of the optic 12, and preferably aligned with the longer axis AL. The first and second haptic mounts 38, 40 are assembled relative to the haptics 14,16 in the same manner; thus, the invention is described with respect to the first haptic mount 38 for purposes of illustrating the invention. The first haptic mount 38 includes an upward extending guide pin 42 having an enlarged cap 44 (shown in FIG. 2 only for purposes of clarity in illustration) at the top thereof The first haptic 14 includes a fixation hole 46, an arced guide track 48, and strut receivers 50. The fixation hole 46 provides a structure at which the first haptic 14 can be sutured or otherwise secured, e.g., via tissue ingrowth, relative to the capsular remnant. The guide track 48 is preferably in the form of a slot and curves along a radius of curvature. The pin 42 of the first mount 38 longitudinally extends within the guide track 48 and is movable between a center location to either end of the arced track as torque is applied to the optic 12, as described further below. Registration indicia 52 can be applied or formed on the first haptic 14 for reference relative to the pin 42 (i.e., pin cap 44) to provide an indication of the angular offset of the optic 12 relative to the first haptic as the pin 42 moves within the guide track 48. The indicia 52 can be as simple as ticks marking off, for example, 10° increments in relative angular offset between the optic and the haptics, or may include actual numerals or other indicia by which to reference the angular offset. The first haptic 14 can be forced over the cap 44 during assembly, and the cap then retains the first haptic from release over the pin 42. The strut receivers 50 receive respective second ends of the struts 18, 20 and provide fixation of such ends relative to the first haptic 14 to retain the struts under tension. The second ends of the struts are mechanically fixed to the haptics during assembly of the haptics the optic. In one exemplar mechanical fixation, the second ends of the struts include barbs or other retainers that are captured within the receivers 50. The assembled struts, fixed end to the end under tension, are displaced to extend outside the patient field of view of the optic, which is preferably 6 mm in diameter. Preferably, the struts are coupled non-radially relative to the optic, and generally coupled along a tangent to the periphery of the optic so that the applied tensile force includes a sufficient torsional component to urge rotation of the optic. Alternatively, where the strut mount is sufficiently large that the first end of the strut is displaced and fixed off the periphery of the optic, then it is preferable that the strut remain parallel to a tangent to the optic. More specifically, if one considers the intersection of the longer axis AL and shorter axis AS of the optic defining four quadrants A, B, C, D, the strut is preferably parallel with a tangent to the optic at the respective quadrant at which it is connected. Such tangential relationship orients the strut to exert torsional force between the optic and the haptics. Even more particularly, it is recognized that the struts are not coupled in an arrangement in which they are oriented in alignment with radii of the optic, as such an orientation would not provide the necessary torsional force between the optic and the haptics to effect rotational adjustment. As indicated, second haptic mount 40, struts 22, 24, and second haptic 16 preferably have like structure, assembly, and operation, as described with respect to the first haptic mount, above described struts, and the first haptic.

The above described assembly provides an optic 12 that is rotationally coupled to the first and second haptics 14, 16. As manufactured, the tensioned struts 18, 20, 22, 24 extending between the optic and the first and second haptics apply a force that is equal on both sides of the long axis AL and thus maintains the lens in a state equilibrium with a net force of zero and a state of torsional stability relative to the AL. In addition, in this embodiment, when the optic, the first and second haptics, and the struts are in the as manufactured configuration, they preferably form a lens having both vertical and horizontal symmetry with one line of symmetry preferably extending through the longer axis AL of the optic which is intended to be placed along the axis of correction and the second line of symmetry extending through the shorter axis AS of the optic. This symmetry relates the structure in a manner that permits logic, relative simplicity, and control to the forces on the optic.

The lens is implanted in the eye as a replacement for the natural crystalline lens. The longer axis AL is aligned with the axis of astigmatic correction. The eye is permitted to heal about the lens, preferably for a period of several weeks, and more preferably 2 to 8 weeks. Due to any of several factors including surgeon error during implantation or movement of the lens as a result of the tissue shrinkage during the healing process, the longer axis AL of the optic can shift relative to the axis of desired corneal astigmatic correction by the time post-operative healing has occurred. In accord with the following, the longer axis AL of the optic can be post-operatively re-aligned with the axis of astigmatic correction.

Figure 3:
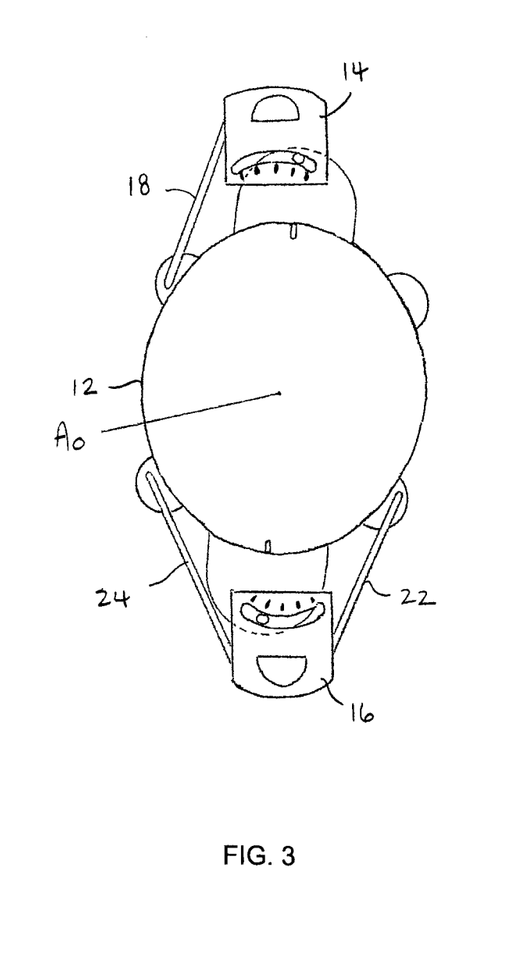
FIG. 3 is a top view of the lens of FIG. 1, in which one of the tensioned struts is removed to effect a defined first rotational displacement of the optic relative to the haptics.
Figure 4:
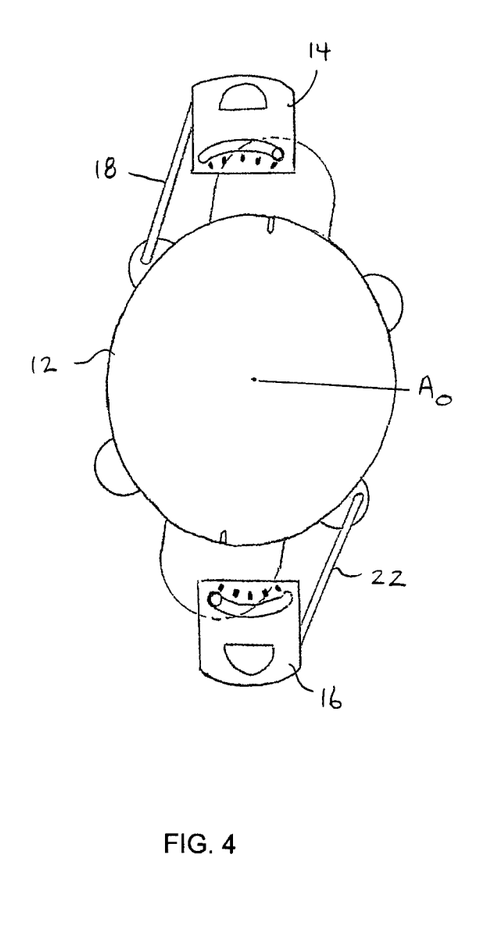
FIG. 4 is a top view of the lens of FIG. 1, in which two of the tensioned struts are removed to effect a defined second rotational displacement of the optic relative to the haptics that is greater than the first rotational displacement.

Turning now to FIG. 3, the struts 18, 20 (shown removed in the figure), 22, 24 are post-operatively individually removable, preferably by the use of energy, such as a laser, but also by surgeon manipulation, such as by microscissors. For laser ablation it is may be advantageous to color, texture, roughen, frost, or otherwise manufacture or treat the struts in manner that causes such structure to absorb laser energy. When appropriate energy or force is applied to a strut 20 to ablate, cut, break, stretch, or otherwise release the tension applied by the strut, the optic 12 is subject to a momentary torsional instability as a result of the imbalance of force exerted on the haptics 14, 16 by the other of the remaining struts 18, 22, 24. This results in rotation of the optic about the optical axis OA in the direction of greater applied torque until remaining struts 18, 22 are decreased in length and strut 24 is stretched in length to result in zero net rotational force. The material and diameter of the struts are chosen so that the zero net rotational force under such conditions occurs after a predetermined number of degrees of rotation. With two pairs of struts each apply opposing torsional force, two of the struts are removable from tension to selectively cause a respective and defined torsional displacement in a defined direction relative to the first and second haptics. In an embodiment, removal of strut 20 causes the optic to rotate relative to the first and second haptics 14, 16 about the optical axis OA to a first clockwise angular displacement, e.g., +10°. Referring to FIG. 4, with the additional removal of strut 24, which was configured to apply torsional force in the same rotational direction as previously removed strut 20, the optic 12 further rotates relative to the first and second haptics 14, 16 about the optical axis OA to a second clockwise angular displacement greater than the first angular displacement, e.g., +20°. Similarly, rather than removing the tension of struts 20 and/or 24, the tension of strut 18 can be removed initially to effect a first counterclockwise angular displacement, e.g., −10°, and subsequently the tension of strut 22 can be removed to effect a greater second counterclockwise angular displacement, e.g., −20°. The appropriate struts are removed to re-align the axis of correction, and confirmation of the correction is referenced relative to the indicia 13. By availing to the capability of the lens, the relationship of the axis of correction AL of the optic relative to the astigmatic aberration can be modified post-operatively, and thus the intended correction can be maximized.

Figure 5:
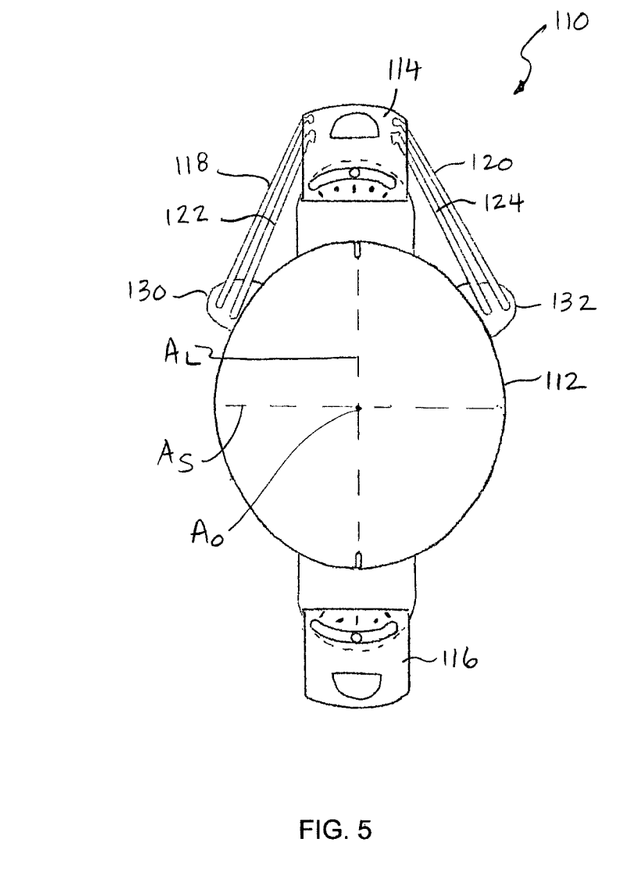
FIG. 5 is a top view of another adjustable toric intraocular lens according to the invention in which, in the as manufactured configuration, tensioned struts extend between the optic and fewer than all of the haptics.

Turning now to FIG. 5, it is appreciated that a lens 110 permitting rotational adjustment of the optic 112 can be effected with tensioned struts 118, 120, 122, 124 attached to one haptic 114 only in the as manufactured and originally as-implanted configuration. As shown, struts 118 and 122 are both coupled to a common first strut mount 130, and provided on one side of the long axis AL, and struts 120 and 124 are both coupled to a common second strut mount 132, and provided on the other side of the long axis AL, with both strut mounts 130, and 132, and all struts 118, 120, 122, 124 residing solely on one side of the short axis AS. Upon removal of strut 120, the optic 112 rotates relative to the first and second haptics 114, 116 about the optical axis OA to a first angular displacement, e.g., +10°. Upon subsequent removal of strut 124, the optic 112 further rotates relative to the first and second haptics 114, 116 about the optical axis OA to a second angular displacement greater than the first angular displacement, e.g., +20°. Similarly, rather than removing struts 120 and/or 124, strut 118 can be removed initially to effect a first angular displacement, e.g., −10°, and subsequently strut 22 can be removed to effect a second greater angular displacement, e.g., −20°. By availing to the capability of the lens, the relationship of the axis of correction AL of the optic relative to the astigmatic aberration can be modified post-operatively, and thus the intended correction can be maximized.

Figure 6:
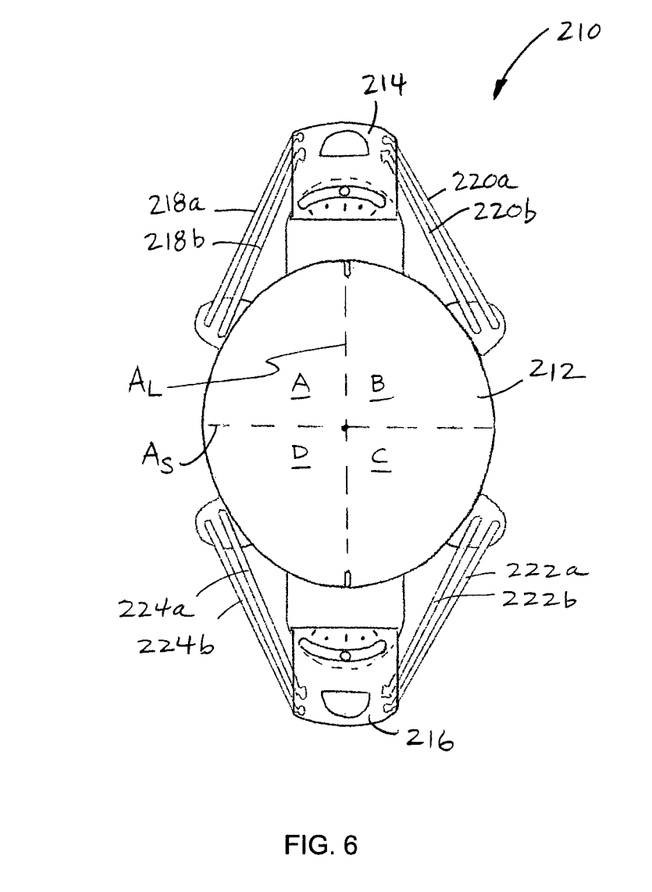
FIG. 6 is a top view of another adjustable intraocular lens according to the invention in which all haptics are connected to more than two opposing struts.

Turning now to FIG. 6, it is recognized that the structural configurations shown in FIGS. 1 and 5 can be combined such that a lens 210 in which pairs of struts 218a, 218b, 220a, 220b, 222a, 222b, 224a, 224b extending from between each of four quadrants A, B, C, D defined on the optic 212 by the longer axis AL and the shorter axis AS and the haptics 214, 216 and one of the first and second haptics 214, 216. The additional number of struts provides a further graduation in the degrees of post-operative angular correction. By way of example only, post-operative angular correction can be made in 2°-5° increments. Another manner of graduating the rotational correction is providing additional haptics about the optic to which the optic is rotationally engaged, and respective removable tensioned struts extending from the optic to the haptics.

Figures 7, 8:
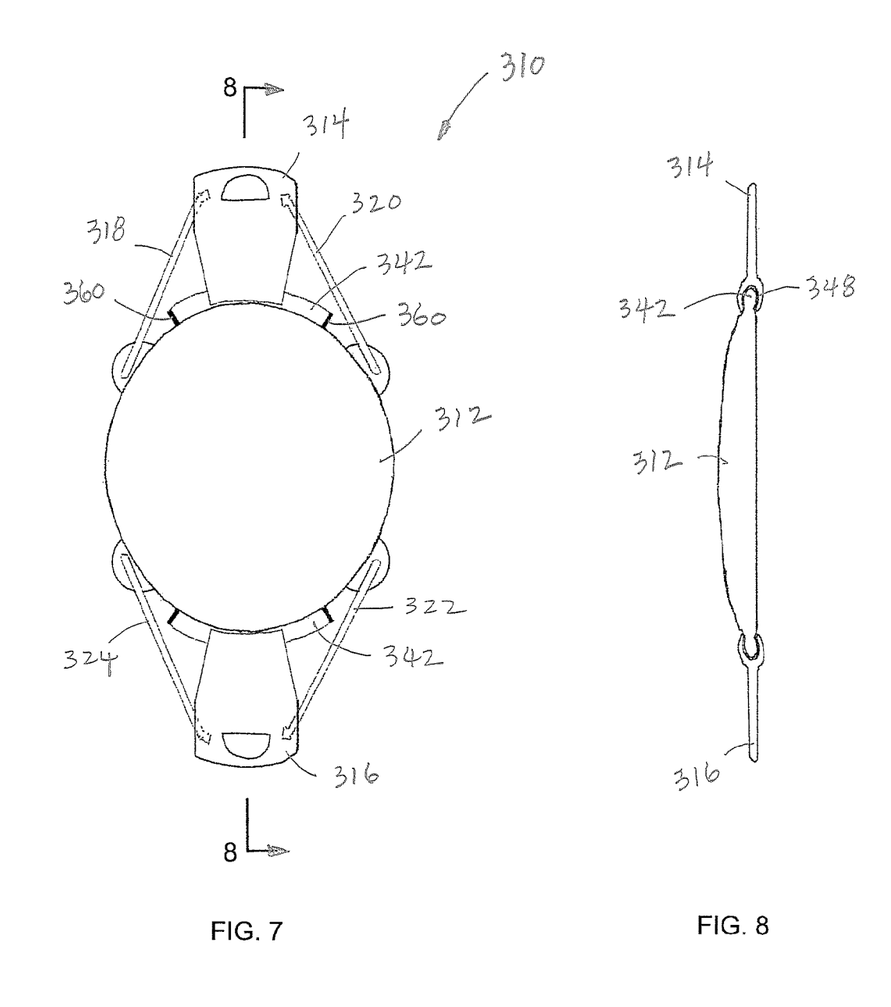
FIG. 7 is a top view of another adjustable intraocular lens showing an alternate movable coupling between the optic and the haptics.
FIG. 8 is a longitudinal section view across line 8-8 in FIG. 7.

Turning now to FIGS. 7 and 8, an embodiment of the lens 310 including an alternative engagement between the optic 312 and haptics 314, 316 that permits the optic to controllably rotationally displace relative to the haptics is shown. The optic 312 defines an at least partially circumferential bead 342 and each haptic defines a C-shaped radially arced channel 348 through the bead 342 can advance when the optic 312 is torqued about the optical axis and relative to the haptics 314, 316. More specifically, the optic preferably includes a bead portion 342 for each haptic, each with stops 360 at opposing ends thereof that limit the travel of bead within the channel, similarly to the ends of the guide slot 48 in a prior embodiments (FIG. 1). Tensioned struts 318, 320, 322, 324 extend between the optic 312 and the haptics 314, 316. As the struts are released from tension, a resulting torsional force is applied to the optic, and the bead on the optic rotates through the channel on the haptic until the net rotational force is zero in the manner described above. Similarly, in yet another embodiment, the optic can include an at least partially circumferential channel, and the haptic can be define a bead over which the channel of the optic can rotationally displace; i.e., the engaging structure of the optic and haptics can be reversed.

Figure 9:
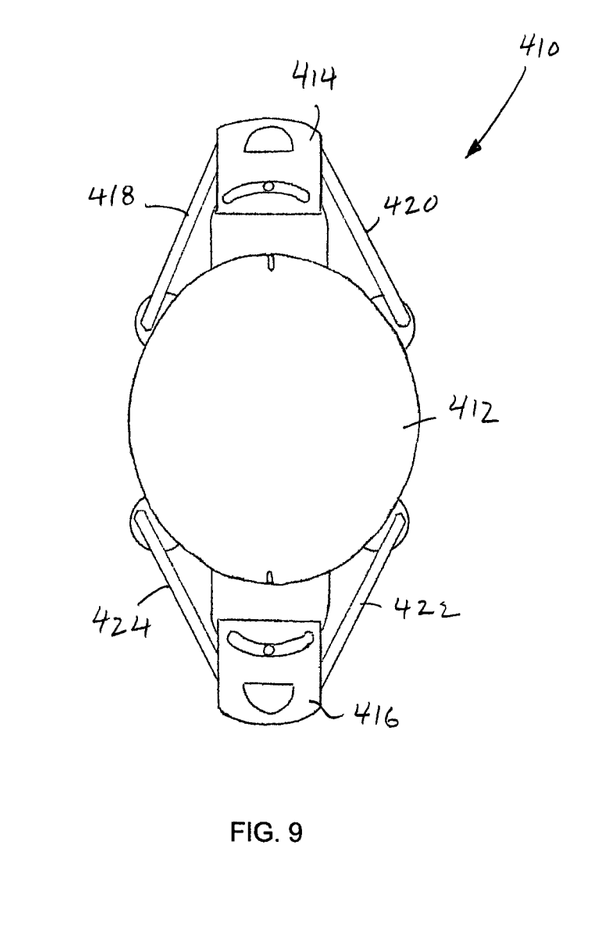
FIG. 9 is a top view of another adjustable toric intraocular lens according to the invention in which, in the as manufactured configuration, the struts may be tensioned to apply a net rotational displacement of the optic relative to the haptics.

Referring now to FIG. 9, another embodiment of a lens 410 according the invention is shown. The struts 418, 420, 422, 424 are comprised of a non-toxic, UV light shrinkable material, which can be activatable by a laser, and which will not release toxic substances on heating. By way of example only, such materials include polyvinyl chloride (Tedlar), polymethylmethacrylate, and a polypropylene under the tradename Prolene, available from Ethicon, Inc. In addition, the disclosure of U.S. Pat. No. 7,837,326 to Jethmalani et al., describing (i) a polymer matrix, and (ii) a modulating composition that is capable of stimulus induced polymerization induced therein, is hereby incorporated by reference in its entirety as teaching a material suitable for use as a light modifiable strut in the present application. The lens 410 is assembled such that the struts 418, 420, 422, 424 initially apply zero net torsional force to the optic 412 relative to the haptics 414, 416. As such, the struts may each initially be in tension or each apply zero tensile force. Then, to initiate a rotational displacement, a laser is used to heat one of the respective struts to cause it to shrink, and is so doing stretch the remaining struts, resulting in a torsional force on the optic 412 with a determined rotational displacement relative to the haptics 414, 416. An additional strut may be shrunk to effect further rotational displacement, or the struts may be shrunk to effect rotation in the opposite direction.

Except as otherwise noted, the components of the lens are preferably fully polymerized and made from a material such as silicone, including MED-6820 Optically Clear Silicone Elastomer, available from NuSil Technology of Carpinteria, Calif. The lens may also be made from a combination of materials, with such materials having a common or different durometers.

There have been described and illustrated herein several embodiments of an intraocular lens. While particular embodiments of the invention have been described, it is not intended that the invention be limited thereto, as it is intended that the invention be as broad in scope as the art will allow and that the specification be read likewise. Thus, while particular coupling of the rotational configuration of the optic relative to the haptics has been described, it will be appreciated that other couplings can be used as well that facilitate the rotation of the optic as tension is released or applied to the joining struts. In addition, while a particular number of haptics and struts have been disclosed, it will be understood that another number of such parts can be used to carry out the invention. Also, while an embodiment is provided with the optic provided with first and second pins and the haptics provided with respective guide tracks, it is appreciated that the parts can be reversed, with the optic provided with the guide tracks and each haptic provided with a pin. Further, while a haptic is shown coupled to a respective pair strut mounts, it is recognized that the strut mounts may be located in alignment with the shorter axis of the optic, and separate struts may extend from a common strut mount toward haptics at opposing sides of the optic. Also, whereas various angular adjustments via modification of a strut, including by removal and shrinking, are disclosed, it is appreciated that the rotational angles previously disclosed are mere examples, and that other rotational adjustments can be made with the modification of each strut, preferably in the range of 2°-–20°, and more preferably between 7°-15°. It will therefore be appreciated by those skilled in the art that yet other modifications could be made to the provided invention without deviating from its spirit and scope as claimed.

What is claimed is:

1. An intraocular lens, comprising:
   a) a tonic optic having an optical axis, a shorter axis and a longer axis;
   b) first and second haptics physically separate and distinct from said optic, said optic rotationally coupled to said first and second haptics; and
   c) a plurality of struts connected and extending non-radially between said optic and at least one of said first and second haptics to rotationally retain said optic in a state of equilibrium,
      wherein at least one of said struts can be modified to temporarily disrupt said state of equilibrium by causing a net torsional force between said optic and said first and second haptics to effect rotation of said optic about said optical axis relative to said first and second haptics.

2. An intraocular lens according to claim 1, wherein:
   said struts are modifiable by light.

3. An intraocular lens according to claim 2, wherein said light modification includes ablation by laser.

4. An intraocular lens according to claim 2, wherein:
   said light modification includes heat shrinkable by laser.

5. An intraocular lens according to claim 1, wherein:
   said lens is symmetrical about said longer axis.

6. An intraocular lens according to claim 5, wherein:
   said lens is symmetrical about said shorter axis.

7. An intraocular lens according to claim 1, wherein:
   modification of a selected one of said struts results in a predetermined clockwise or counterclockwise rotation of said optic relative to said first and second haptics.

8. An intraocular lens according to claim 1, wherein:
   one of said optic and said first haptic is provided with a pin, and the other said optic and said first haptic is provided with a guide track having a length extending along a radius a curvature, and said pin is movable along said length when said net torsional force is applied.

9. An intraocular lens according to claim 1, further comprising:
   indicia provided to said lens to represent the rotational orientation of said longer axis relative to said first and second haptics.

10. An intraocular lens, comprising:
a) a toric optic having an optical axis, a shorter axis and a longer axis, wherein said longer axis defines an axis of astigmatic correction;
b) at least one haptic physically separate and distinct from said optic, said optic rotationally coupled to said at least one haptic;
c) a first strut coupled in tension and extending non-radially between said optic and said at least one haptic on a first side of said longer axis; and
d) a second strut coupled in tension and extending non-radially between said optic and said at least one haptic on a second side of said longer axis, wherein said second strut applies tension in opposing force to said first strut such that said optic is retained in a state of equilibrium relative to said at least one haptic,
wherein when said tension applied by said first strut is disrupted from between said optic and said at least one haptic, a net torsional force is effected between said optic and said at least one haptic to alter a rotational orientation of said optic about its optical axis relative to said at least one haptic.

11. An intraocular lens according to claim 10, wherein:
said optic and said at least one haptic are symmetrical about at least one of said longer axis and said shorter axis.

12. An intraocular lens, comprising:
a) a toric optic having an optical axis, a short axis and a long axis, wherein said longer axis defines an axis of astigmatic correction;
b) a first haptic and a second haptic separate and distinct from said optic, said optic rotationally coupled to said first and second haptics;
c) a first strut extending non-radially between said optic and said first haptic on a first side of said long axis and applying a first tension therebetween;
d) a second strut extending non-radially between said optic and said first haptic on a second side of said long axis and applying a second tension therebetween, wherein said second tension is equal and opposite said first tension;
e) a third strut extending non-radially between said optic and said second haptic on said first side of said long axis and applying a third tension therebetween; and
f) a fourth strut coupled extending non-radially between said optic and said second haptics on said second side of said long axis and applying a fourth tension therebetween, wherein said fourth tension is equal and opposite said third tension,
said optic retained in a state of equilibrium relative to said first and second haptics,
wherein when said first tension is disrupted, a net torsional force is effected between said optic and said first and second haptics to first alter a rotational orientation of said optic about its optical axis relative to said first and second haptics.

13. An intraocular lens according to claim 12, wherein:
when said fourth tension is disrupted, an additional net torsional force is effected between said optic and said first and second haptics to second alter a rotational orientation of said optic about its optical axis relative to said first and second haptics.

14. An intraocular lens according to claim 13, wherein:
in said second altered rotational orientation, said optic is rotated by an additional 2°-20° relative to said first and second haptics.

15. An intraocular lens according to claim 12, wherein:
said rotational orientation can be selectively chosen to be in either a clockwise or a counterclockwise orientation.

16. An intraocular lens according to claim 12, wherein:
in said first altered rotational orientation, said optic is rotated by 2°-20° relative to said first and second haptics.

17. An intraocular lens according to claim 12, wherein:
in said first altered rotational orientation, said optic is rotated by 7°-15° relative to said first and second haptics.

18. An intraocular lens according to claim 17, wherein:
in said second altered rotational orientation, said optic is rotated by an additional 7°-15° relative to said first and second haptics.

19. An intraocular lens according to claim 12, wherein:
said first tension on said first strut is disruptable by laser energy.

20. An intraocular lens according to claim 12, wherein:
said first and second haptics are coupled to said optic in alignment with said longer axis.

* * * * *